United States Patent [19]
Kaessmann et al.

[11] Patent Number: 5,597,581
[45] Date of Patent: Jan. 28, 1997

[54] CHITOSAN FOIL FOR WOUND SEALING AND PROCESS FOR ITS PREPARATION

[75] Inventors: Hans-Jürgen Kaessmann, Hamburg; Karl W. An Haak, Am Hedreisch 25, D-44225 Dortmund, both of Germany

[73] Assignee: Karl W. An Haak, Dortmund, Germany

[21] Appl. No.: 397,219

[22] PCT Filed: Jun. 28, 1994

[86] PCT No.: PCT/EP94/02104

§ 371 Date: Apr. 14, 1995

§ 102(e) Date: Apr. 14, 1995

[87] PCT Pub. No.: WO95/01808

PCT Pub. Date: Jan. 19, 1995

[30] Foreign Application Priority Data

Jul. 9, 1993 [DE] Germany .................. 43 22 956.5

[51] Int. Cl.⁶ .................................................. A61F 13/00
[52] U.S. Cl. ........................................... 424/449; 604/305
[58] Field of Search ................. 604/305; 514/21, 514/55; 424/447, 445, 446, 448, 449

[56] References Cited

U.S. PATENT DOCUMENTS

| | | | |
|---|---|---|---|
| 4,488,564 | 12/1984 | Grollier et al. | 424/81 |
| 4,532,134 | 7/1985 | Malette . | |
| 4,572,906 | 2/1986 | Sparkes et al. | 514/21 |
| 4,659,700 | 4/1987 | Jackson . | |
| 4,867,150 | 9/1989 | Gilbert . | |
| 5,035,893 | 7/1991 | Shioya et al. | 424/447 |
| 5,384,125 | 1/1995 | DiPippo et al. | 424/417 |

FOREIGN PATENT DOCUMENTS

| | | |
|---|---|---|
| 0138385 | 4/1985 | European Pat. Off. . |
| 0295777 | 12/1988 | European Pat. Off. . |
| 0460774A2 | 12/1991 | European Pat. Off. . |
| 2922012 | 12/1979 | Germany . |
| 3321446 | 5/1984 | Germany . |
| 4322956C2 | 1/1995 | Germany . |

Primary Examiner—David Isabella
Assistant Examiner—David J. Cho
Attorney, Agent, or Firm—Herbert Dubno; Jonathan Myers

[57] ABSTRACT

The invention relates to a foil of chitosan for wound sealing. According to the invention this foil contains glycerin as an elasticity enhancing additives and has a perforated surface promoting gas exchange.

5 Claims, 1 Drawing Sheet

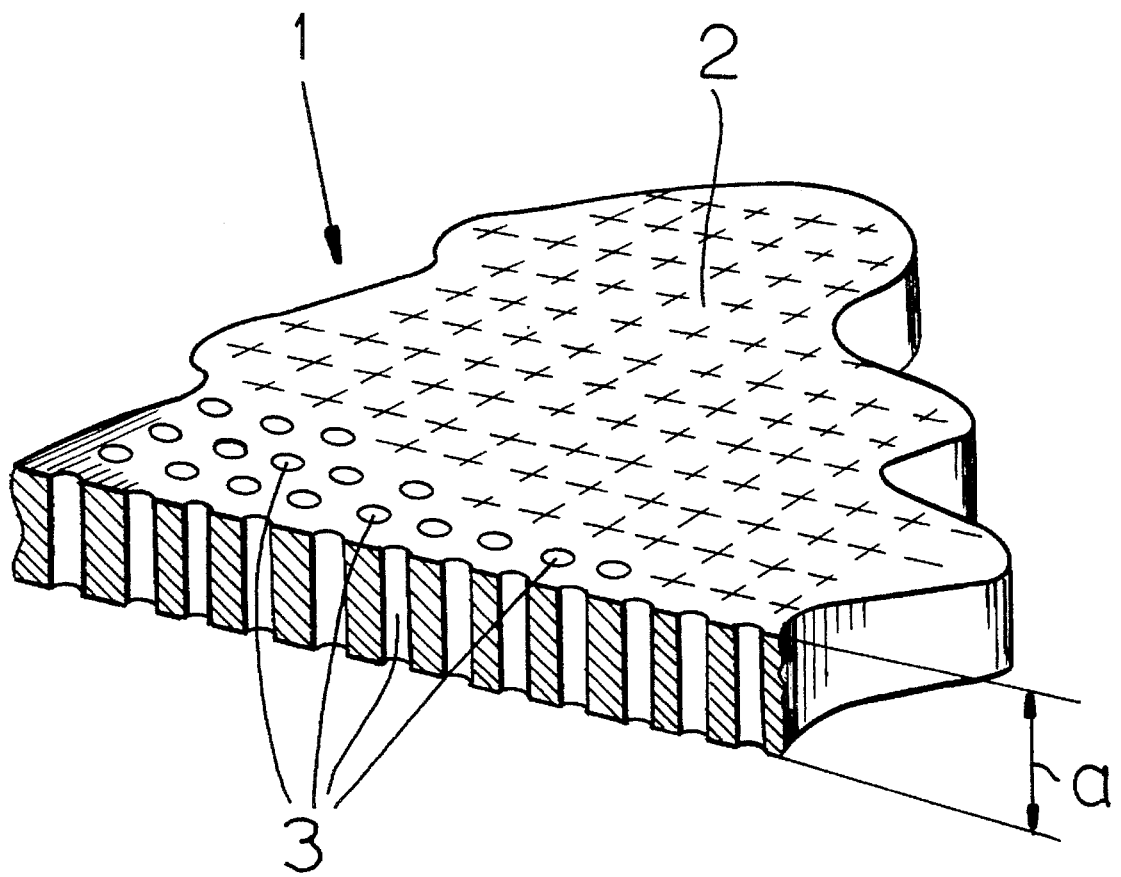

CHITOSAN FOIL FOR WOUND SEALING AND PROCESS FOR ITS PREPARATION

BACKGROUND OF THE INVENTION

The invention relates to a foil of chitosan for wound dressing.

Chitosan with the structure formula

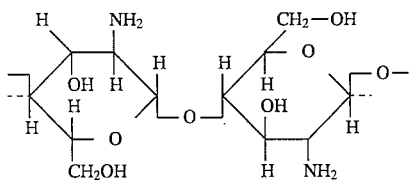

is a deacetylation product of chitin which can be obtained on a technical scale from the shells of crabs, crawfish and other shell-encased organisms. Chitosan is soluble in diluted solutions or organic acids, for instance in three to five percent acetic acid and can be processed from this solution to foils, plates, gels, sprays and powders, according to known precipitation processes (Manufacturing Chemist 10 (1984) pages 47 to 52).

There are various possibilities to use chitosan as a biocompatible substance in field of medical techniques. From High-Tech 7 (1988) pages 29 to 37 it is known to use chitosan foils for the wound-sealing of burns. On a wounded surface of the human body the foil behaves like a heterologous skin substitute, which not only protects the wound against undesired external mechanical action, but also creates a favorable physiological environment for healing. As a rule the foil is left as a seal on the wound until towards the end of the wound-healing phase the foil is spontaneously rejected. It has also passed through the shrinking process, respectively the reduction process of the wound and has become a kind of scab, underneath of which the injured skin was able to regenerate.

The chitosan foil has a certain air permeability. Through tests which are not part of the prior art it has been found that the oxygen-permeability of the chitosan foil is heavily dependent on the relative humidity of the environment. The oxygen permeability is drastically reduced when the relative humidity decreases. Especially when wounds having a large surface are sealed the sufficient breathing of the wound is not insured. However the gas exchange through a wound dressing is important, because a high $CO_2$ pressure reduces the pH value and slows down the healing process, and in addition a low oxygen concentration makes possible the proliferation of anaerobic bacteria. Further the use of the known chitosan foil in the dressing of wounds with a large surface is limited due to the fact that the dry foil is relatively brittle. Large-surface wound-sealing on curved body parts, such as elbow, chin, heel, knee or shoulder portions is used rarely or not at all, because of the brittleness of the known chitosan foil.

SUMMARY OF THE INVENTION

It is the object of the invention to indicate a chitosan foil for wound sealing which can be used over large surfaces also in body parts which are generally difficult to dress.

In order to achieve this object the invention teaches that the foil contains glycerin as an elasticizing additive and has a perforated surface which stimulates the gas exchange. According to the invention the foil is provided with breathing openings which are distributed evenly over the surface, in large numbers per surface unit. The diameter of the breathing opening should be larger than 100 μm. The perforations have namely to be so small that the wound secretions can not pass through and be pressed onto the foil surface. The surface has to remain dry and is not allowed to assume a gel-like consistency. The addition of glycerin increases the elasticity of the foil.

According to a preferred embodiment of the invention the foil is charged with an active substance which assists the wound treatment and which is released during the enzymatic decomposition of chitosan. The addition of Australian tea tree oil has proven to be particularly effective. The Australian tea tree oil is obtained through gentle vapor distillation from the leaves of the tea tree (*Melaleuca alternifolia*). At the same time the etherial oil enhances the bactericidal and fungicidal action of the chitosan. Further it is advantageous when the foil contains cod liver oil as an additional active substance which protects the skin against keratinization, whereby such an additive is also effective against psoriasis.

With the chitosan foil of the invention it is possible to seal wounds caused by skin removal, burns, abrasions, bruises and defects, even on large surfaces, as well as particularly the chronic Ulcus cruris venosus, whereby the wound sealed against external damaging factors can create itself its optimal healing environment, especially also in the case of infected wounds. The outer surface of the chitosan foil remains hard and dry after contact with the wet wound, due to permanent air drying, while the bottom surface assumes a gel-like consistency due to partial absorption of the wound secretions. This leads to a wound cleaning, as well as to a further elastic adjustment of the foil to the irregularities of a wound surface. The physiologically important wet environment of the wound is not destroyed during the exudative healing phase. At the transition area between the wet and dry zones, i.e. at the wound edge, an adherence effect of the foil to the intact skin, but not to the wound, is created, so that the wound dressing can be painlessly removed or in certain cases changed and replaced again. The chitosan foil influences the hemostasis in the sense that it stops the bleeding, which can be observed as a favorable effect immediately after the wound appeared. Advantageous is also the bactericidal and fungicidal effect, which partially can be explained by the acid components resulting from the molding solution used during the course of the foil production. The chitosan foil prevents excessive protein loss in extensive burns. Just like any other foreign body in the wound, the chitosan foil activates the granulation capability of the connective tissue, as well as the capillary multiplication, which leads to the acceleration of the healing process of the wound. The foil made of animal, regenerating raw substances can also be used as the carrier for a locally acting anaesthetic solution, in order to alleviate the initial wound pain.

Further it is the object of the invention to create a process for the production of the described foil. According to the process of the invention, a casting solution is prepared from finely ground chitosan and a diluted organic acid, this casting solution is drawn into a film and the film is dried thereby forming a foil, whereby to the casting solution, prior to its further processing into a foil, glycerin is added in amounts of approximately 10 ml glycerin to 1 l casting solution and whereby breathing openings are stamped into the foil, this way providing the foil with a perforated surface enhancing the gas exchange. In a further embodiment the invention teaches that the casting solution be mixed with an active substance assisting in the treatment of the wound, preferably with Australian tea tree oil. The etherial tea tree oil acts as a natural disinfectant with special fungicidal action. The dispersion of the glycerin and tea tree oil which per se are not soluble in diluted organic acid is surprisingly possible in the viscous chitosan-casting solution. A stable emulsion is formed.

BRIEF DESCRIPTION OF THE DRAWINGS

FIG. 1 is a perceptive sectional view showing the structure of the wound dressing in accordance with the invention.

DETAILED DESCRIPTION OF THE PREFERRED EMBODIMENT

Subsequently the invention is described with the aid of a drawing illustrating only one embodiment example. The sole FIGURE shows the cutout of a wound-sealing foil 1 made of chitosan. Normally it has a thickness a of 100 μm to 500 μm. Preferred is a foil thickness of 200 μm to 500 μm. In the case of infected wounds the preferred thickness of the foil lies in the upper range of the above-indicated parameter range. In excessively infected wounds a foil of more than 0.5 mm thickness can be used. The chitosan foil contains glycerin as an elasticity-enhancing additives. The glycerin addition lies in the range of 10 ml/1 l casting solution. Besides the foil can contain an active substance which assists the healing of the wound and which is released during the enzymatic decomposition of the chitosan. In the embodiment example the foil contains Australian tea tree oil in the amount of approximately 1 ml to 1 l of casting solution. It is visible from the drawing FIGURE that the chitosan foil has a perforated surface 2 which enhances the gas exchange. The perforated surface contains breathing openings 3 in great number per surface unit. The maximal diameter of the breathing openings equals 100 μm.

The chitosan foil represented in the drawing FIGURE can be used for the sealing of extensive wounds and has the already explained characteristics. It can be considered as a heterologous skin substitute, which is also more interesting from the economical point of view, than the heterologous skin substitutes obtained from mammals (e.g. pig, mouse, etc) or through skin production based on growing cell cultures.

We claim:

1. An oxygen-permeable, breathable foil through which wound secretions cannot pass, for sealing a wound to promote exudative healing of said wound, said oxygen-permeable, breathable foil capable of sealing wound secretions and at the same time permitting gas exchange between said wound and a surface of said oxygen-permeable, breathable foil, which consists essentially of:

a dried porous film consisting of:
   (a) chitosan;
   (b) glycerine as a suppleness promoter; and
   (c) an agent for promoting wound healing which is liberated from the dried porous film by enzymatic decomposition; wherein the oxygen-permeable, breathable foil has a thickness of at least 200 microns and a surface provided with breathing openings of a maximum diameter of 100 microns capable of promoting gas exchange therethrough between said wound and said surface of said oxygen-permeable, breathable foil thereby permitting the wound to heal and capable of sealing the wound to prevent escape of wound secretions.

2. The oxygen-permeable, breathable foil defined in claim 1 wherein the foil thickness is 200 to 500 microns.

3. The oxygen-permeable, breathable foil defined in claim 1 wherein the foil thickness is 500 microns.

4. The oxygen-permeable, breathable foil defined in claim 1, wherein the agent for promoting wound healing is Australian tea tree oil.

5. The oxygen-permeable, breathable foil defined in claim 1, wherein the agent for promoting wound healing is cod liver oil.

\* \* \* \* \*